US 8,601,666 B2

(12) United States Patent
Ortiz

(10) Patent No.: US 8,601,666 B2
(45) Date of Patent: Dec. 10, 2013

(54) METHOD OF MAKING AN ANATOMICAL SOCKET

(76) Inventor: Rodolfo Marlo Vazquez del Mercado Ortiz, Guadalajara (MX)

( * ) Notice: Subject to any disclaimer, the term of this patent is extended or adjusted under 35 U.S.C. 154(b) by 865 days.

(21) Appl. No.: 12/297,568

(22) PCT Filed: Apr. 17, 2006

(86) PCT No.: PCT/IB2006/002851
§ 371 (c)(1),
(2), (4) Date: Oct. 17, 2008

(87) PCT Pub. No.: WO2007/119095
PCT Pub. Date: Oct. 25, 2007

(65) Prior Publication Data
US 2009/0105844 A1    Apr. 23, 2009

(51) Int. Cl.
*B21D 39/03*    (2006.01)

(52) U.S. Cl.
USPC ............... 29/428; 623/33; 623/36; 623/27

(58) Field of Classification Search
USPC ................... 29/428; 623/33, 36, 37
See application file for complete search history.

(56) References Cited

U.S. PATENT DOCUMENTS 6,077,300 A * 6/2000 Sabolich et al. ............... 623/37
6,991,657 B1 * 1/2006 Price, Jr. ...................... 623/33

* cited by examiner

*Primary Examiner* — David Bryant
*Assistant Examiner* — Moshe Wilensky
(74) *Attorney, Agent, or Firm* — Michael L. Greenberg, Esq.; Greenberg & Lieberman, LLC

(57) ABSTRACT

An anatomical socket is fashioned to attach to an amputated limb, which can be a median between the amputated limb and the prosthesis device. The method produces, based on specific measurements of a user, an anatomical socket that provides the user with cosmesis, a greater range of motion, a better gait and comfort. The socket has a low upper rim to allow for the greatest mobility of the hip joint. The socket is produced of a durable and smooth plastic. The socket fits in a secure, yet removable manner to the prosthesis. The method disclosed herein takes precise measurements of the wearer's limb to provide for optimal fitting and comfort.

6 Claims, 5 Drawing Sheets

METHOD OF MAKING AN ANATOMICAL SOCKET

FIELD OF THE INVENTION

The present invention is a method of making an anatomical socket for the thigh, more specifically, a method of making a socket for prosthesis having a seamless fit, wherein the connection from the socket to the posterior and anterior lateral of the user is not noticeable through clothing and the like.

BACKGROUND OF THE INVENTION

There are people in many parts of the world that have amputated limbs due to a variety of circumstances. Many of these people choose to use prostheses on their legs or arms that have been amputated to give them greater mobility or increased use of their amputated limb. An inherent problem with some prostheses is a rubbing or chaffing where the prosthesis connects to a moving joint, such as a hip for an amputated leg. This means that there is a problem with the sockets of the prostheses. The problem with such prostheses is that they are cast from standard molds in many cases. The molds, while made in certain generic sizes, do not fit many users properly. There is a need for a method of making a socket for a prosthesis that results in a socket for a prosthesis that will not rub or chaff where the prosthesis connects to a moving joint.

Additionally, because an amputated limb often has a greater degree of muscular atrophy than a non-amputated limb, the amputated limb has decreased muscle mass. This can lead to a situation in which a person with an amputated limb has one leg or arm that can easily be identified as the amputated limb—even through clothing. When a typical prosthesis is fitted on an amputated limb that has decreased muscle mass, the prosthesis is chosen based on the muscular mass of the amputated limb, and thus, the prosthesis fitted on the amputated limb has a narrower circumference than the non-amputated limb; and also, the prosthesis merely exacerbates the ability of the amputated limb area appearing narrower through clothing. There is a need for a method of making a socket for a prosthesis that takes into account the typical smaller circumference of an amputated limb so that the prosthesis made cannot be easily identified as the amputated limb because of its size.

Also a prosthesis for the thigh is often placed high on the ischial complex, and thus, is uncomfortable for the wearer. There is need for a method of making a socket for a prosthesis that can fit a user comfortably, while the prosthesis will still communicate with the ischial complex. Moreover, the high placement on the ischial complex makes the shape of the prosthesis easily identifiable through clothing and the like. The user of a prosthesis wants to appear to the public as if a prosthesis is not being worn at all, and placement of the prosthesis high on the ischial complex defeats this purpose. The high placement of the prosthesis decreases mobility of the hip or other joint as well. Thus, there is a need for a method of making a socket for a prosthesis that can communicate with the ischial complex properly, in a natural way, allowing increased mobility.

Therefore a need has been established for a method of making an anatomical socket for a prosthesis which allows the user less chaffing or rubbing than existent methods, appears through clothing to be of the same size as the non-amputated limb, and fits lower than existent sockets to allow greater mobility.

SUMMARY OF THE INVENTION

The present invention is a method of making an anatomical socket that attaches to an amputated limb, and preferably in the thigh. The present invention is also a method of making an anatomical socket to serve as a median between the amputated limb and a prosthesis. The anatomical socket made by the method of the present invention provides the user with cosmesis, a greater range of motion, a better gait (if used on a prosthesis for a leg), and comfort without chaffing or rubbing.

In the preferred embodiment of the present invention, a method is described for creating a socket to be used as a medial ramus containment socket. The socket fits lower than conventional ischial containment sockets as measured per the anterior, posterior and medial walls. The lower fit of the socket allows for greater cosmesis in the gluteal and lateral areas, in such a manner that it is very hard to see any protrusion trim lines of the socket. The lower anterior wall also allows for a full range of hip flexion. Additionally, the medial wall is high enough to contain the medial aspect of the ischial ramus while being low enough to avoid pressure over the ischial ramus.

The socket made by the method of the present invention allows for a lower fit in the anterior, posterior, and medial regions, and thus allows for the femur to be in a better adducted position to give a narrow base gait, which would be closer to a non-amputated gait. The lower fit produced by the method eliminates a proximal weight bearing area, allowing for a quasi-hydrostatic weight bearing area over the rest of the amputated limb, adding to the comfort of the user. The lower fit also increases comfort because the higher fits cause excessive pressure in the proximal area of the socket.

DETAILED DESCRIPTION OF THE PREFERRED EMBODIMENT (S)

Figure 1:
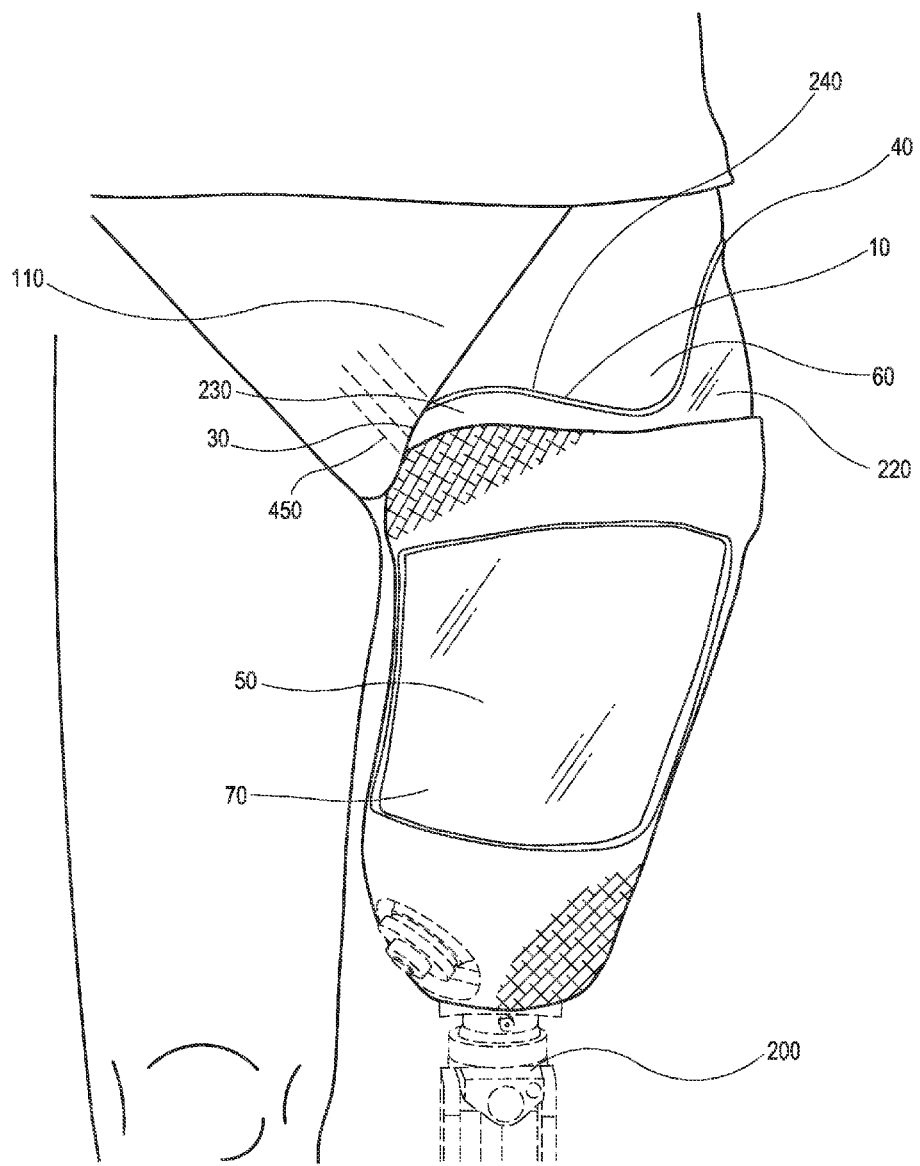
FIG. 1 shows a frontal view of a user wearing the socket made by the method of the present invention.

The present invention is a method for making an anatomical socket that communicates with a prosthesis to hold an amputated limb. The present invention is a method that produces a socket based on specific measurements of a user's body. The method produces a socket, based on measurements of the wearer's limb, having four anterior surfaces—anterior end 10, posterior end 20, medial end 30, and lateral end 40. Further, the present invention produces a socket having a lower portion 50 that is generally conventional in that it allows for the user's limb 60 to be received and held via suction. The bottom 70 of lower portion 50 is also fairly conventional in that it can communicate via all conventional means with artificial limbs that typically attach at the bottom of a conventional anatomical socket. However, the method of production of the anatomical socket is unique.

In general, anatomical ischial containment sockets need to fit high up on the user's thigh, or else, they will not allow for desired control of the artificial limb attached to the anatomical socket. The present invention produces a socket with the anterior end 10 much lower on the user's limb 60 than in conventional ischial containment anatomical sockets. Further, the present invention is a method of producing a socket with the posterior end 20 also much lower on the user's limb 60 than in conventional ischial containment anatomical sockets. Moreover, the method of the present invention produces a socket with the medial end 30 high enough to support the ischial ramus while medial end 30 is also much lower on the user's limb 60 than in conventional anatomical ischial containment sockets. The anterior end 10, posterior end 20, and medial end 30 are still able to provide the user with a range of motion and control equal or surpassing conventional anatomical ischial containment sockets because of unique measurements that are part of the method of the present invention, resulting in a superior socket. The unique measurements affect how horizontal type forces hold the socket produced by the present invention onto the user's limb 60.

Figure 4:
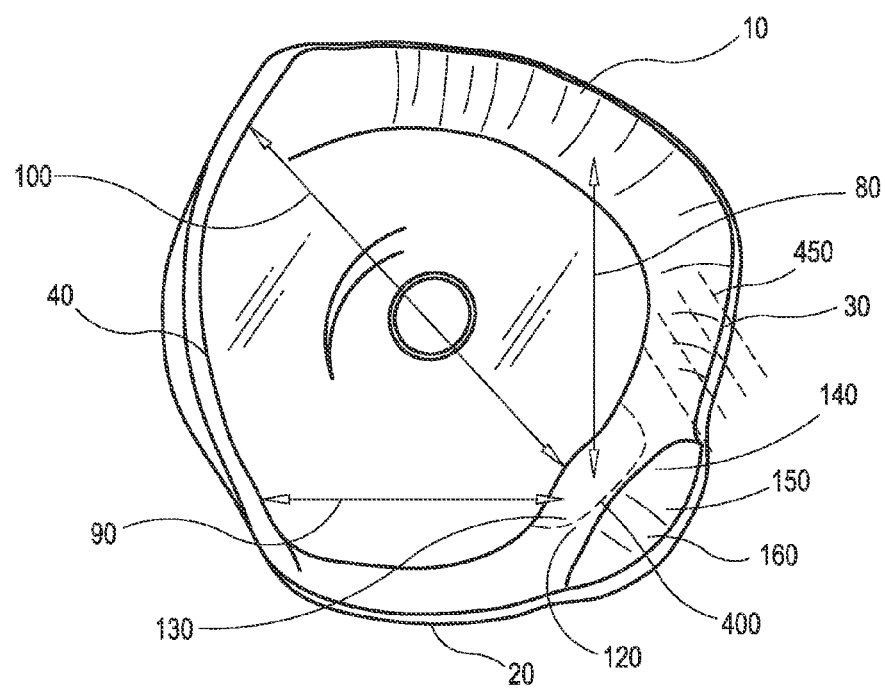
FIG. 4 shows a top view of the socket made by the method of the present invention.
Figure 5:
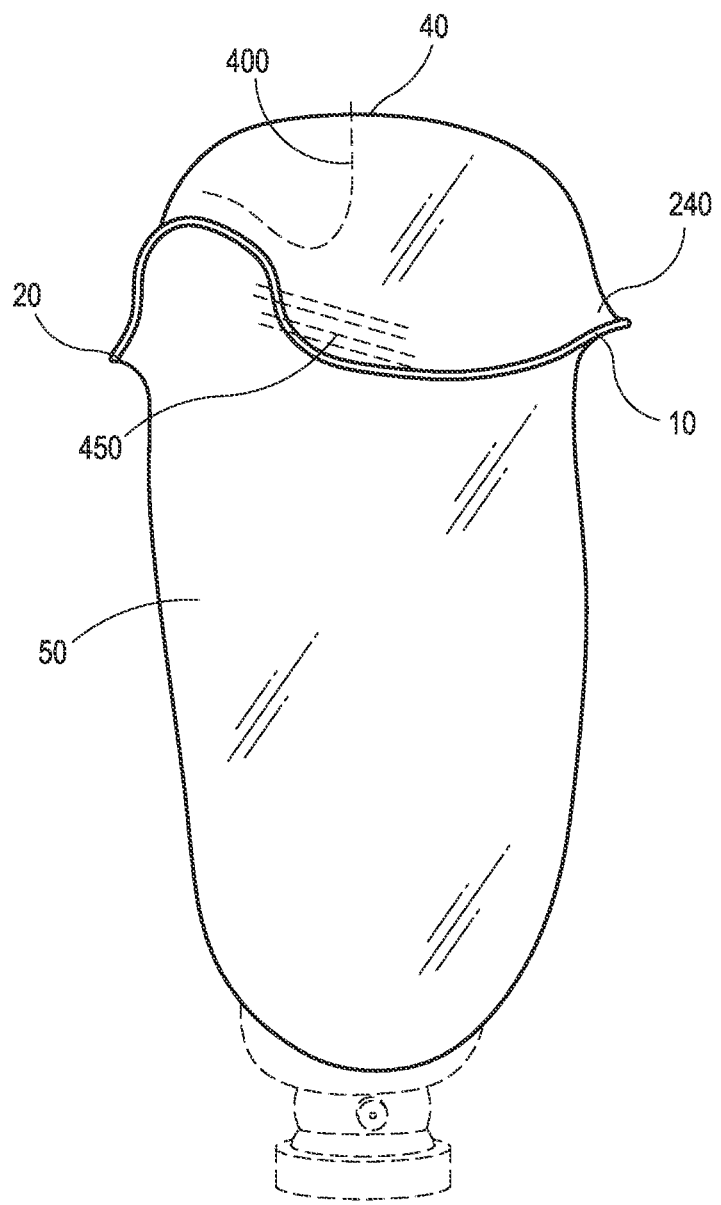
FIG. 5 shows a medial side view of a user wearing the socket made by the method of the present invention.

Specifically, the present invention provides a method for making a socket so that a first force 80 is present from anterior to posterior of a socket, such that first force 80 exists between anterior end 10 and medial end 30, as shown in FIG. 4. The present invention provides a method for making a socket so that a second force 90 is present from lateral to medial of a socket made by the method of the present invention, such that second force 90 exists between posterior end 20 and medial end 30, as shown in FIG. 4 as well. The resultant first force 80 and second force 90 combine together to achieve a resultant force 100 that exists between lateral end 40 and medial end 30. Thus, even though anterior end 10, posterior end 20, and medial end 30 have been lowered in comparison to conventional anatomical sockets, the socket made by the method of the present invention is fully functional in providing range of movement.

In fact, because the anterior end 10 of the socket made by the method of the present invention has been lowered, the user is able to move their limb 60 up and closer to the their abdomen if desired, as there is not a high anterior wall to apply underside pressure to the user's abdomen. Similarly, because the posterior end 20 has been lowered, the user is able to move the user's limb 60 up and closer to their back if desired, as there is not a high posterior wall to apply underside pressure to the user's buttocks. Moreover, the prosthesis made by the method of the present invention, having a lower medial end 30, is able to relieve much if not all of the discomfort associated with pressure from an anatomical ischial containment socket on the user's ischial ramus.

The prosthesis made by the method of the present invention also has specialized modifications, in addition to its unique method of creating anterior end 10, posterior end 20, medial end 30, and lateral end 40. Posterior end 20 is measured per user so that it does not rise higher than the bottom of the buttocks. By being fashioned to reside at the break between the user's buttocks and limb 60, as well as slightly curving outward from the user, posterior end 20 does not appear to exist under the user's clothing. The desire of the user to appear without having an anatomical socket in place is achieved with the posterior end 20.

Another specialized method of the present invention is the formation of the anterior end 10, which is made to curve outward from the user. As with the posterior end 20, the anterior end 10 is measured per user so that it does not rise higher than the beginning of the user's limb 60. In fact, the anterior end 10, in some portions, is below the point at which the user's limb 60 attaches to the user's pelvic girdle 110. By making the product of the method of the present invention to reside at or below the break between the user's pelvic girdle 110 and limb 60, as well as slightly curving outward from the user, anterior end 10 does not appear to exist under the user's clothing. The desire of the user to appear without having an anatomical socket in place is achieved with the anterior end 20.

Yet another specialized modification of the method of the present invention is fashioning the medial aspect of the ischial ramus containment socket 120, which is a subpart of the medial end 30. Medial aspect of the ischial ramus containment socket 120 is formed between a ledge 130 and a wall 140. Ledge 130 is formed to support the medial aspect of the ischial ramus of the user analogous to a shelf for the medial aspect of the ischial ramus to sit on while the prosthesis fashioned by the method of the present invention is worn. Wall 140 serves to ensure that the user's medial aspect of the ischial ramus does not move from ledge 130 and is 10-20 degrees from the vertical plant so that it forms a 70-80 degree angle with ledge 130. Between ledge 130 and wall 140 is the medial aspect of the ischial ramus containment socket in which the user's medial aspect of the ischial ramus sits. Thus, containment socket 120 maintains the user's medial aspect of the ischial ramus in a fixed position relative to the prosthesis fashioned by the method of the present invention. This is desirable because movement of the medial aspect of the ischial ramus relative to an anatomical socket causes a great deal of discomfort.

The socket made by the method of the present invention is specially modified for comfort of the user's ischial ramus as well because it has an ear-like member 150 on the backside of wall 140. While wall 140 is directed to maintaining the medial aspect of the ischial ramus in place for control and comfort, ear-like member 150 is concerned with comfort on the medial side of the ischial ramus. Ear-like member 150 has a curved top hemisphere 160 so that the top and sides of wall 140 do not dig into the medial side of the ischial ramus.

The lateral end 40 of the socket rises conventionally along the user's limb 60, however, lateral end 40 also has a curved upper portion to achieve cosmesis and allow the user to as much movement of limb 60 as possible in a lateral fashion.

The present invention is a method of producing the socket of a durable and smooth plastic, which in the preferred embodiment is clear, but in other embodiments could be produced in different colors. The socket fits in a secure, yet removable manner to a prosthesis 200, and holds the user's limb 60 without chaffing or excessive rubbing.

In summary, FIG. 1 shows a frontal view of a user wearing a socket made by the method of the present invention on the user's limb 60. As is shown, the present invention is a method to fit the socket in a cylindrical manner over the end of the user's limb 60 up toward the user's pelvic girdle 110. The present invention is a method to fit the socket higher on the outer curvature of the user's hip 220, than on the user's inner thigh 230. The method produces a socket that has a bottom 70 of lower portion 50 with a smaller diameter than the upper open portion 240 (as defined by anterior end 10, posterior end 20, medial end 30, and lateral end 40). The bottom 70 of lower portion 50 fits in a secure yet removable manner to a prosthesis 200 as is shown. The present invention is a method of making a socket that supports the user's limb 60 without adding unnecessary pressure to the user's hip, end of the limb 60, or the inner thigh. Additionally the present invention is a method of making a socket shaped like the thigh of a conventional non-amputated leg so that the shape of the prosthesis fashioned by the present invention cannot be easily distinguished through clothing.

Figure 2:
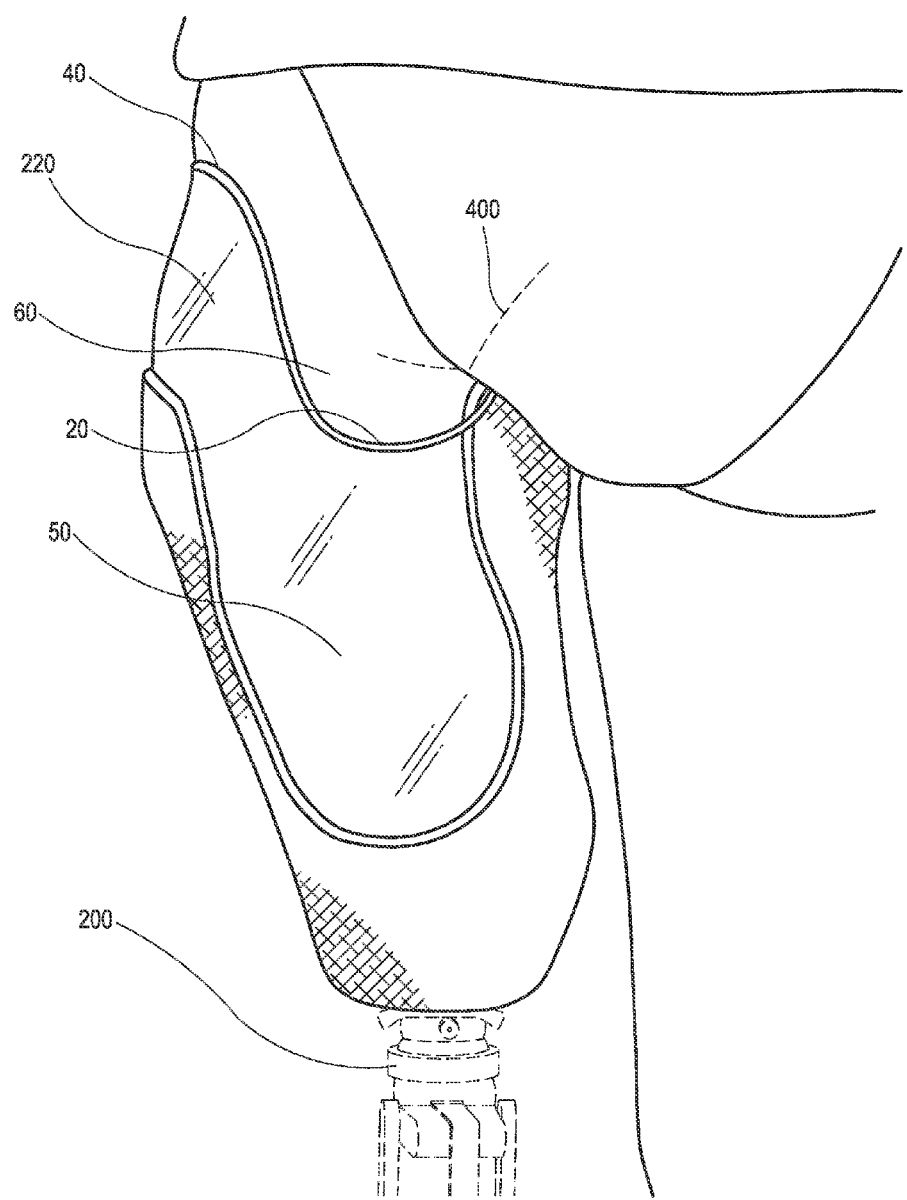
FIG. 2 shows a rear view of a user wearing the socket made by the method of the present invention.
Figure 3:
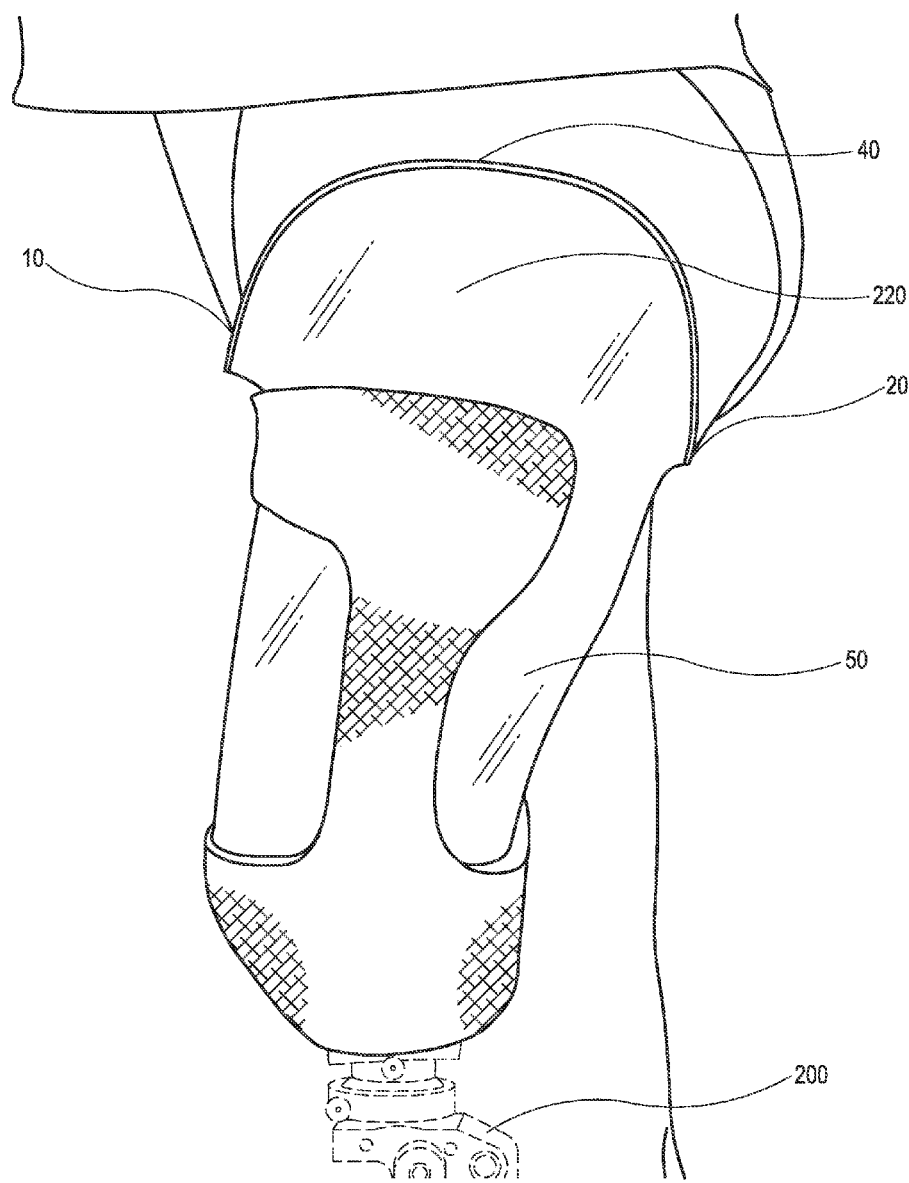
FIG. 3 shows a lateral side view of a user wearing the socket made by the method of the present invention.

FIG. 2 shows a rear view of a user wearing the product of the method of the present invention on a limb 60. The present invention is fashioned to fit higher on the outer curvature of the hip and upper thigh than it is across the back of the limb 60. As is shown in FIGS. 1 and 2, the prosthesis as fashioned by the present invention allows for total mobility of the hip joint. FIG. 3 shows a lateral side view of the socket produced by the method worn by a user on a limb 60. The curvature of the socket is higher on the lateral side of the limb 60 than on the front or back of the thigh.

The present invention is a method that produces a prosthesis that is preferably intended for use as a medial aspect of the ischial ramus containment socket. However, in alternate methodologies of the present invention, the socket made by the method of the present invention can be made for use on other joints or amputated limbs. The lower fit of the socket produced by the method of the present invention allows for greater cosmesis in the gluteal and lateral areas, in such a manner that it is very hard to see any protrusion trim lines of the socket. Additionally, the medial end 30 is low enough to avoid pressure over the ischial ramus, or the blood vessels of the amputated limb 60.

Preferred steps for the method of making the socket are as follows:

Form anterior end 10 at the level of the wall 140 or below.

Measure medial end 30 ¼-½ inch below the ischial ramus exit.

Dimension posterior 20 "U" shaped from ischial ramus level or below depending on the anatomical gluteal fold of each amputee.

Form lateral end 40 above the greater trochanter wrapping around the anterior-lateral proximal corner, and covering the posterior-lateral (wallet hollow).

Wall 140 is measured to have a width, as measured anterior to posterior, of one to two inches. This measurement tends to vary depending on the personal anatomical structure of each person. Wall 140 has a height of ½-1½ inches.

Ledge 130 is measured to have a width, as measured anterior to posterior, matching wall 140. Ledge 130 is measured to have a width, as measured medial to lateral, of ½-1 inch.

Preferred features of the method of making the socket are as follows:

Wall 140 is fashioned to a more anterior position over the medial aspect of the ischial ramus, from behind the adductors muscles to posterior aspect of the ischial ramus. It is made to be parallel to the ischial ramus. There is no weight bearing over the ischial ramus and ischial tuberosity. Within the present method, the wall 140 provides rotational control.

The present invention is a method of producing, based on a user's individual measurements, a rigid container frame made of carbon fiber with trim lines lower than the flexible inner socket to provide flexibility in the proximal brim area, window in the anterior below the rigid strut, lateral and medial rigid struts, and posterior opening.

The ischial ramus (400), shown as a dotted line, can be seen in FIG. 2, FIG. 3, FIG. 4, and FIG. 5. The adductor muscles (450), shown as four dotted lines, can be seen in FIG. 1 and FIG. 5.

Having illustrated the present invention, it should be understood that various adjustments and versions to the method might be implemented without venturing away from the essence of the present invention. The present invention is not limited to the methodology and resulting embodiments as described above.

I claim:

1. A method for making an anatomical socket for a user's limb, comprising:

fashioning an anterior end that angles down from the user's limb's medial end, and then angles sharply upward toward the user's limb's distal end;

placing a lateral end adjacent to said anterior end, said lateral end higher than said anterior end, said lateral end curving around the hip of the user's limb;

placing a medial end adjacent to said anterior end, said medial end having a wall fashioned to an anterior position over a medial aspect of the ischial ramus of the user from behind adductor muscles to a posterior aspect of the ischial ramus such that said wall is parallel to the ischial ramus and such that there is no weight bearing over the ischial ramus and ischial tuberosity; and placing a posterior end adjacent to said lateral end and said medial end, said posterior end having a lower height than said anterior end, said posterior end above the user's thigh;

wherein said anterior end and said medial end exert a first force on the user's limb, while said posterior end and said medial end exert a second force on the user's limb, such that said lateral end and said medial end have a resultant force there between, wherein the recited relationships of the anterior end, lateral end, medial end, and posterior end to the user's anatomy occur when the user's limb is oriented in a standing position.

2. The method of claim 1, wherein said posterior end is fashioned to fit the user's limb no higher than the user's gluteal fold.

3. The method of claim 1, wherein said anterior end is made to have a top curvature to fit the medial aspect of the user's ischial ramus.

4. The method of claim 1, wherein said anterior end is made to have a ledge and wall to receive the user's ischial ramus there between.

5. A method for making an anatomical socket for a user's limb, comprising:

fashioning an anterior end that angles down from the user's limb's medial end, and then angles sharply upward toward the user's limb's distal end;

placing a lateral end adjacent to said anterior end, said lateral end higher than said anterior end, said lateral end curving around the hip of the user's limb;

placing a medial end adjacent to said anterior end, said medial end having a wall fashioned to an anterior position over a medial aspect of the ischial ramus of the user from behind adductor muscles a posterior aspect of the ischial ramus such that said wall is parallel to the ischial ramus and such that there is no weight bearing over the ischial ramus and ischial tuberosity; and placing a posterior end adjacent to said lateral end and said medial end, said posterior end having a lower height than said anterior end, said posterior end above the user's thigh;

wherein at least said anterior end; said lateral end, said medial end, or said posterior end has a top trim curvature, wherein the recited relationships of the anterior end, lateral end, medial end, and posterior end to the user's anatomy occur when the user's limb is oriented in a standing position.

6. The method of claim 5, wherein said posterior end is fashioned to fit the user's limb no higher than the user's gluteal fold.

\* \* \* \* \*